(12) United States Patent
Fisher, III et al.

(10) Patent No.: US 7,440,878 B2
(45) Date of Patent: Oct. 21, 2008

(54) VIRTUAL MODELS

(75) Inventors: Robert Burns Fisher, III, Scotland (GB); Petko Faber, Leonberg (DE); Timothy Campbell Lukins, Scotland (GB)

(73) Assignee: The University Court of the University of Edinburgh (GB)

( * ) Notice: Subject to any disclaimer, the term of this patent is extended or adjusted under 35 U.S.C. 154(b) by 449 days.

(21) Appl. No.: 11/123,699

(22) Filed: May 5, 2005

(65) Prior Publication Data

US 2005/0278156 A1    Dec. 15, 2005

Related U.S. Application Data

(63) Continuation of application No. PCT/GB03/04765, filed on Nov. 5, 2003.

(30) Foreign Application Priority Data

Nov. 5, 2002    (GB) ................................ 0225716.1

(51) Int. Cl.
  *G06F 17/00* (2006.01)
  *G06T 17/00* (2006.01)
(52) U.S. Cl. ............................. 703/2; 703/7; 707/104.1; 702/155

(58) Field of Classification Search .................... 703/2, 703/7; 700/110; 702/19, 155; 707/104.1
See application file for complete search history.

(56) References Cited

U.S. PATENT DOCUMENTS

| | | | |
|---|---|---|---|
| 6,594,538 B1 * | 7/2003 | Graham et al. ............... 700/110 |
| 6,873,724 B2 * | 3/2005 | Brand ......................... 382/154 |
| 2001/0027456 A1 * | 10/2001 | Lancaster et al. ......... 707/104.1 |
| 2003/0097219 A1 * | 5/2003 | O'Donnell et al. ............ 702/19 |

FOREIGN PATENT DOCUMENTS

WO    WO 2004/042660 A3    5/2004

* cited by examiner

*Primary Examiner*—Thai Phan
(74) *Attorney, Agent, or Firm*—Ganz Law, P.C.

(57) ABSTRACT

A method of generating a virtual model of an object, comprising the step of constructing a fused model to represent the variation of the shape of the object in a plurality of configurations. In the method, position variation vectors may be calculated which describe the variation of a plurality of points in the fused model from their mean positions over all the configurations of the object; the position variation vectors may be assigned a weighting factor which represents a measure of their probabilistic confidence; a weighted covariance matrix may be constructed to represent the variations; the weighted covariance matrix may be operated on to obtain shape variation vectors representing the weighted direction and magnitude of variations; such that the fused model may describe how the shape of the object varies as a function of the shape variation vectors scaled by a shape parameter.

26 Claims, 4 Drawing Sheets

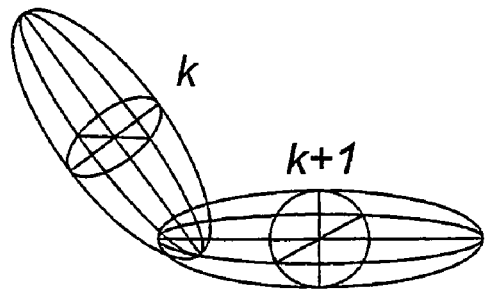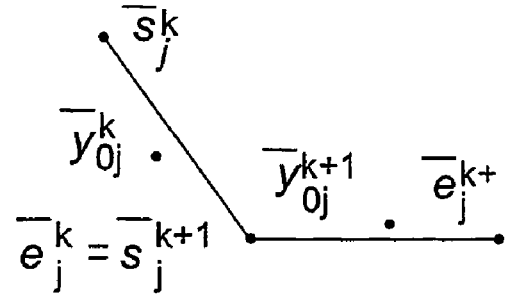
Fig. 1a  Fig. 1b
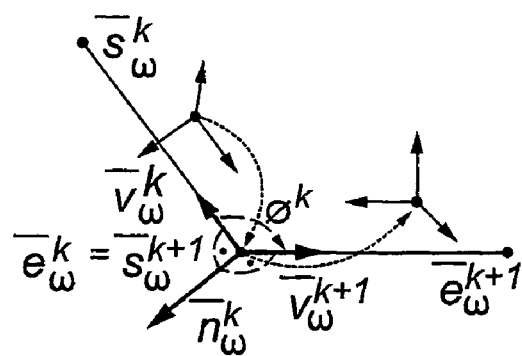
Fig. 2

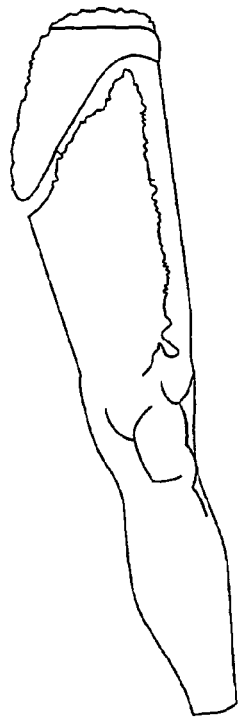
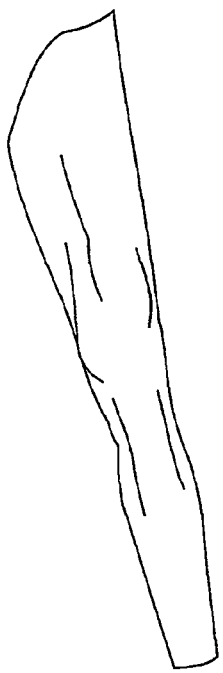
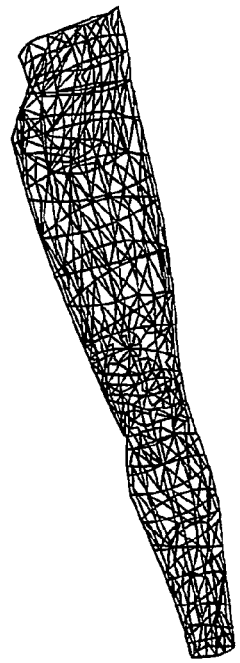
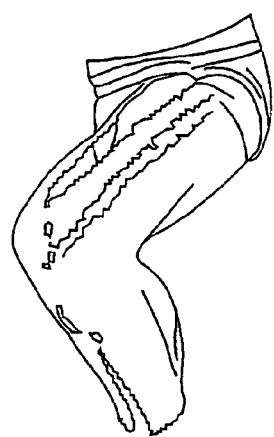
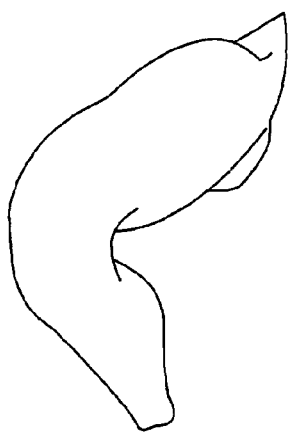
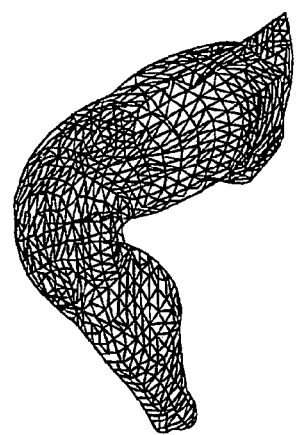
*Fig. 3a*   *Fig. 3b*   *Fig. 3c*
Figure 3: a) raw data patches of a left leg, b) appropriate modified generic models, c) triangular meshes of the generic models.

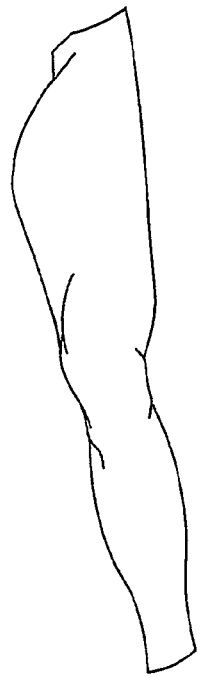 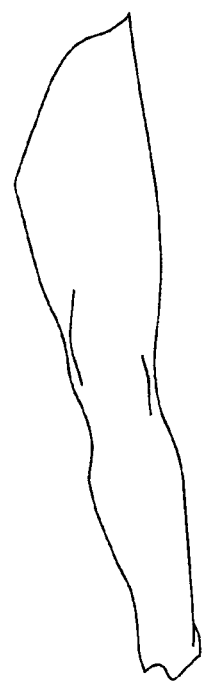 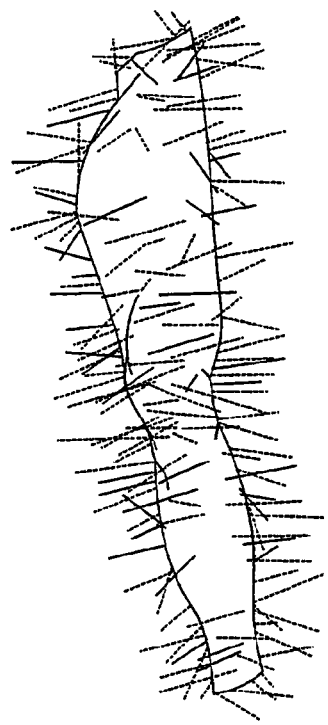
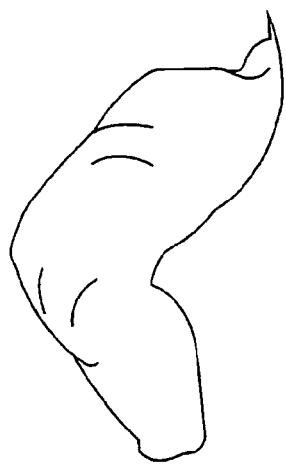 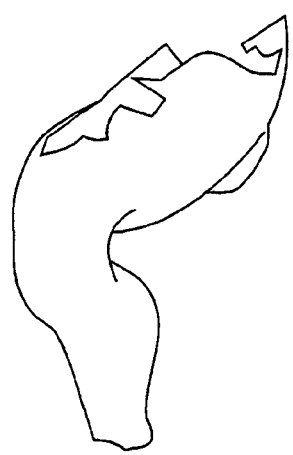 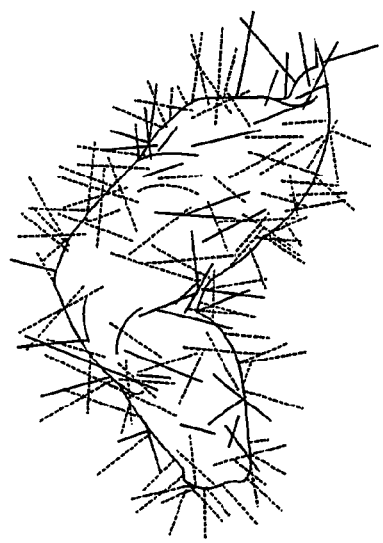
*Fig. 4a*  *Fig. 4b*  *Fig. 4c*
Figure 4:conformed data patch, b) conformed data patch where only $\vec{y}_{ij}^k$ with $\alpha_{ij}^k > 0$ are used to visualize the triangular mesh and C) vertex normals after the conformation process. The direction of the normals is colour coded: white - the vertex normal points to the view point, black - normal is pointing away.

Figure 5: fused model of the leg, b) fused model where only $\vec{y}_{ij}^{k}$ with $\alpha_{ij}^{k} > 0$ are used to visualize the trianguler mesh and c) estimated vertex normals based on the concept of *Gouraud* shading.

VIRTUAL MODELS

RELATED APPLICATIONS

This application is a continuation of International PCT application No. PCT/GB2003/004765, filed Nov. 5, 2003, entitled VIRTUAL MODEL GENERATION, which claims priority to and the benefit of Great Britain patent application number GB0225716.0, filed Nov. 5, 2002, the entire disclosures of which are hereby incorporated by reference as if recited in full herein for all purposes.

BACKGROUND OF THE INVENTION

The present invention relates to virtual models, in particular to a method of generating a virtual model of an object, a virtual model of an object and a virtual model of an object embodied on a record medium.

The modeling of realistic virtual human models is of importance to both research and industrial communities. Realistic modeling of individual human characters is essential for advanced multimedia, augmented reality, teleconferencing, and situation planning for plastic surgery or even a hair cut.

Early efforts in the area of virtual human models focused on interpolation techniques that modeled a body as a set of simple shapes, and using physical laws to dynamically model the motions of the body. However, common motions such as walking are too complex to calculate in this manner.

Problems in this regard led to methods being based on anatomical know-how. A human body is a collection of complex rigid and non-rigid components, such as skeleton, muscles, skin, and hair. Of these, the musculature has attracted a lot of attention because it is the most complex anatomical system that determines the surface form.

Muscles typically consist of different kinds of tissue, allowing some parts to be contracted and others not. Depending on their state of contraction, muscles have different shapes and thus, they influence the surface form in different ways.

Thus, anatomical models have been constructed, which typically involve a biomechanical model to represent muscle deformation. These methods provide an accurate representation of the major structures of the body, but take up a lot of computational power, which means ability to animate the models in real time is compromised.

As a way of overcoming these limitations, an example based method has been proposed, in which a model of some body parts in different poses with the same underlying mesh is generated. One example based method would be to construct the shape of a specific person by mapping 2D photographs onto a generic 3D model.

More recent attempts along these lines have focused on constructing a skeleton and aligning this with a set of captured poses, and linking polygonal models to the skeleton. This method is implemented by observing the positions of markers captured during initial scanning of the object. The main drawback of this technique is that a large number of markers are needed to produce an accurate model, and shape manipulation of body parts in the sense of muscle deformation is not possible.

Efforts have also been made to model humans by representing the variation of shape and texture, in which new configurations of an object can be modeled by forming linear combinations of a number of prototypes.

Thus, there is a need to create realistic virtual human models in a way that is less time consuming and computationally expensive than methods using currently available technologies. Furthermore, there is a need for the creation of realistic virtual human models that can be used with interactive applications, particularly where it is required to animate or modify the model in real time.

SUMMARY OF THE INVENTION

According to a first aspect of the present invention there is provided a method of generating a virtual model of an object, comprising the step of constructing a fused model to represent the variation of the shape of the object in a plurality of configurations, in which:

position variation vectors are calculated which describe the variation of a plurality of points in the fused model from their mean positions over all the configurations of the object:

the position variation vectors are assigned a weighting factor which represents a measure of their probabilistic confidence;

a weighted covariance matrix is constructed to represent the variations;

the weighted covariance matrix is operated on to obtain shape variation vectors representing the weighted direction and magnitude of variations;

such that the fused model describes how the shape of the object varies as a function of the shape variation vectors scaled by a shape parameter.

Preferably, the operation on the covariance matrix to get the shape variation vectors is a singular value decomposition, and the shape variation vectors are found by converting the eigenvectors of a factorized matrix into 3-vectors.

Optionally, the shape variation vectors are found by considering the variations as being constrained to a single vector orthogonal to a longitudinal axis of the object.

This may give a more robust description of the deformation when the variation in the shape vectors is relatively large, due to, for example, the mis-alignment of conformed vertices.

Preferably, a function is calculated that maps the joint angles and gravity vector to the shape parameter.

Preferably, the function provides a linear relationship.

Preferably, the fused model is constructed from a conformed data set, obtained by performing the steps of:

obtaining a set of range data from an object in a plurality of configurations;

fitting the transformed range data to a generic model; and transforming the range data from each configuration to a common reference frame.

Preferably, the range data represents the object by defining a plurality of vertices, the positions of which are described by vectors.

Preferably, the generic model is a generic mesh model.

Preferably, the method further comprises the step of performing a complete model reassembly, wherein the shape of the intersection between two reassembled subcomponents is accommodated as the mean of their shared vertices.

Preferably, the shape of the object in the fused model is further scaled by an exaggeration parameter.

Preferably, the exaggeration parameter defines a factor by which the magnitude of the modeled deformation of the object is multiplied.

Preferably, a plurality of objects forms a composite object and the relative positions of the objects are calculated so that a combined model can be constructed to represent the composite object.

Preferably, the objects are assumed to be rigidly connected by joints positioned at a start and an end position of each object;

an axis is defined for each object which runs from a start position as averaged over all configurations to an end position as averaged over all configurations;

the end point of one object is assumed to be commensurate with the start point of an adjacent object; and a complete model of the composite object is constructed in which the mean relative positions of the objects are combined with a specific configuration set, the set defining the specific configurations for each object in the composite object.

Preferably, a region of intersection between two adjacent rigid subcomponents defines an overlap region, the shape of which is derived as the mean shape.

Preferably, the axis is the main axis of an ellipsoid which is fitted to the fused model of the object, and the start and end points are determined from an estimation of the closest intersection points between the axes of the approximating ellipsoid and the ellipsoids fitted to the vertices of the neighboring objects.

Preferably, the composite object is part of a human body and the objects making up the composite object are parts of the body.

The present application is not limited to the modeling of a human body. Animal bodies and other jointed mechanisms can be modeled using the techniques of the present invention.

Preferably, the model is used to represent the deformation of muscle tissue in the body to create a virtual model of how a body deforms as it moves.

According to a second aspect of the present invention, there is provided model generation means to generate a virtual model of an object, comprising fused model construction means to construct a fused model suitable for modeling the variation of the shape of the object in a plurality of configurations, in which:

position variation vectors are calculated which describe the variation of each vertex from its mean position over all the configurations of the object;

the position variation vectors are assigned a weighting factor which represents a measure of their probabilistic confidence;

a weighted covariance matrix is constructed to represent the variations;

the weighted covariance matrix is operated on to obtain shape variation vectors representing the weighted direction and magnitude of variations; and such that the fused model describes how the shape of the object varies as a function of the shape variation vectors scaled by a shape parameter.

Preferably, the fused model construction means further comprises singular value decomposition means suitable to operate on the covariance matrix, and eigenvector conversion means to convert the eigenvectors of a factorized matrix into 3-vectors, so as to find the shape variation vectors.

Optionally, the fused model construction means further comprises means to derive a single vector orthogonal to a longitudinal axis of the object, to which the variations are constrained.

This may give a more robust description of the deformation when the variation in the shape vectors is relatively large, due to, for example, the mis-alignment of conformed vertices.

Preferably, the model generation means further comprises:

data gathering means to obtain a set of range data from an object in a plurality of configurations;

transformation means to transform the range data from each configuration to a common reference frame;

and fitting means to fit the transformed range data to a generic model.

Preferably, the range data represents the object by defining a plurality of vertices, the positions of which are described by vectors.

Preferably, the generic model is a generic mesh model.

Preferably, the model generation means is further suitable for performing a complete model reassembly wherein the shape of the intersection between two reassembled subcomponents is accommodated as the mean of their shared vertices.

According to a third aspect of the present invention, there is provided a data carrier embodying data which is capable of co-operating with a computer apparatus to perform the method of the first aspect.

According to a fourth aspect of the present invention, there is provided a data carrier embodying data which is capable of co-operating with a computer apparatus to form the model generation means of the second aspect.

According to a fifth aspect of the present invention, there is provided a virtual model of an object generated using the method of the first aspect of the present invention.

According to a sixth aspect of the present invention, the virtual model of the fourth aspect is provided on a computer usable medium.

It will be appreciated that any or all the steps of the method described in the first aspect of the present invention can be performed by the model generation means of the second aspect, and a virtual model according to the fourth aspect of the invention may be created using any or all of the steps of the method described in the first aspect of the invention, or using the model generation means described in the second aspect.

BRIEF DESCRIPTION OF THE DRAWINGS

The present invention will now be described, by way of example only, with reference to the accompanying drawings, in which:

FIGS. 1A, 1B, and 2 illustrate stages in the method of the present invention; and FIGS. 3A, 3B, 3C, 4A, 4B, 4C, 5A, 5B, and 5C show experimental results illustrating the implementation of the present invention.

DETAILED DESCRIPTION OF THE INVENTION

Figures 5A, 5B, 5C:
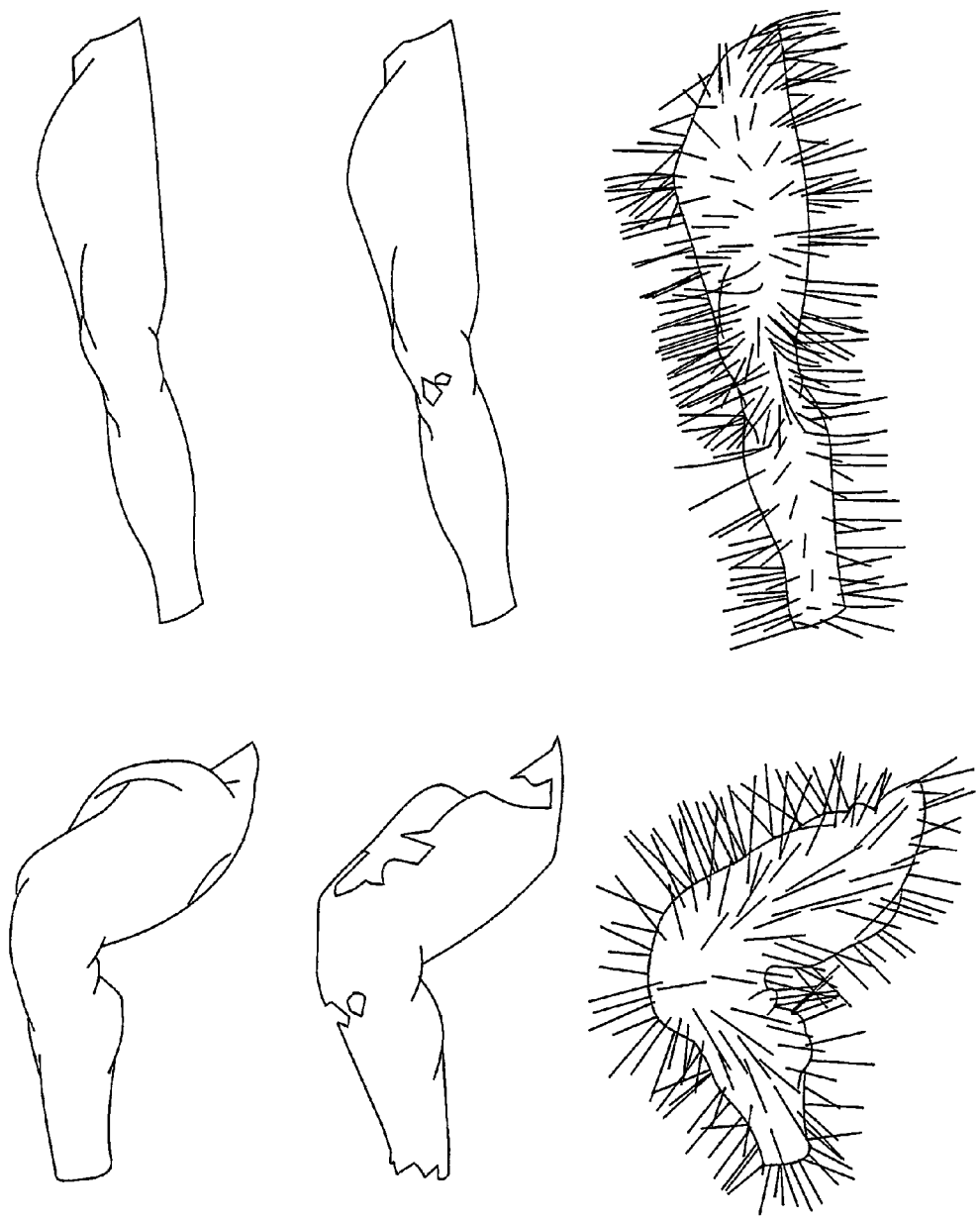

The process described herewith assumes that there is a triangular mesh that describes the typical shape, such as an average human body. When modeling a particular human's shape, several 3D data shapes are obtained and the generic mesh is deformed to fit each data set. These individual fits are the conformed meshes (e.g. [1], [2]) used as input into the shape modeling process described here.

All merged meshes have the same vertices, but the vertices are in slightly different positions arising from the conformation process applied to different views.

Each vertex in the conformed mesh has a weighting factor that indicates the reliability of the node. The vertices of the conformed meshes may be dependent on the observed 3D data in which case the weight factors will usually be non-zero. If there was no nearby data to influence shape changes in the conformed mesh, then the weight factors are usually zero. Noisy vertices may also have their weights reduced. The use of weights in the conformed mesh allows the fusion of multiple partial observations of the surface into a single model. This is essential as most 3D data acquisition systems will be unable to obtain data from all of a surface, for example due to blind spots and occlusion.

In the present invention, we assume that we have 3D data from enough views to complete a model, and that there are at least 2 observations of each data point. We also assume that each view has consistent shape, which may vary as a function of joint angle, and that each model subcomponent instance is represented by a triangular mesh with the same topology, and where each vertex represents approximately the same surface point on the original object.

Above, the invention is described as being for the creation of a model for an object, with a plurality of objects forming a composite object. In the case where the present invention is applied to creating a model of a human body, the object, also called a subcomponent of the model, may correspond to a particular limb, or to a particular segment of a limb, and the composite object is that represented by the model, which can be the entire human body, or a subdivision thereof, for example, a torso or a head.

The invention can be used to enable easy and cheap creation of virtual clones of specific individuals that can be animated in computer games, film and television, e-commerce, advertisements and many other media applications.

In the following description of the invention, various terminological definitions and variables shall be used, some of which are defined as follows:

The input is a set J of conformed meshes for each subcomponent with identical topology and vertex identifiers, but different vertex positions.

Each input mesh $j \in J$ is a collection of segmented subcomponents K connected by joints $\Theta$ and has different joint angles $\{\phi_j^k\}$.

The j-th conformed instance of the k-th subcomponent has $i=[1 \ldots V_k]$ measured vertices $\{\vec{y}_{ij}^k\}$.

Each measured vertex $\{\vec{y}_{ij}^k\}$ has a confidence weight $\alpha_{ij}^k \in [0, 1]$, where 0 means no confidence and 1 perfect confidence.

i—over vertices in a conformed subcomponent model.
j—over instances of the vertex obtained from different conformations to different captured data sets.
k—over different rigidly connected subcomponents.
$\vec{y}_{ij}^k$—raw conformed vertex positions in the original coordinates of instance j.
$Y_i^k = \{\vec{y}_{ij}^k, j=[1 \ldots J]\}$—set of raw conformed vertex positions in the original co-ordinates.
$\vec{\alpha}_{ij}^k$—subcomponent vertices transformed to lie in common co-ordinate system $\omega(k)$.
$A_i^k = \{\vec{\alpha}_{ij}^k, J=[1 \ldots J]\}$ set of transformed subcomponent vertices in common co-ordinate system $\omega(k)$.

Construction of a fused model for a body or body portion takes these steps:

1. Remove the rigid transformations between each set of subcomponent instances to place all data for a subcomponent in the same reference frame.
2. Identify and re-weight outliers.
3. Construct the fused subcomponent models defining vertex positions as a function of deformation parameters.
4. Infer the function that maps from the joint parameters to the deformation parameters.
5. Estimate the skeleton relations.
6. Reconstruct the generic model based on relative positions of the individual components.
7. Create instances of the fitted model as a function of joint parameters and musculature exaggeration.

These steps shall now each be described in more detail.

Removal of Transformations

The goal is to transform all instances j of subcomponent k into the same reference frame. Choose $\omega(k) \in [1 \ldots J]$ as the reference subcomponent instance. Let $$\vec{y}_{0j}^k = \frac{1}{V_k} \sum_i \vec{y}_{ij}^k$$

be the mean vertex position of the $j^{th}$ data instance of the $k^{th}$ component. Let $\vec{z}_{ij}^k = \vec{y}_{ij}^k - \vec{y}_{0j}^k$ be the direction vector of each vertex i relative to the mean position. Define the 3×3 scatter matrix for the vertices in view j as:

$$D_j^k = \frac{\sum_i \alpha_{i\omega(k)}^k \alpha_{ij}^k \vec{z}_{i\omega(k)}^k \left(\vec{z}_{ij}^k\right)^T}{\sum_i \alpha_{i\omega(k)}^k \alpha_{ij}^k} \quad (1)$$

The matrix can $D_j^k$ can be factored by singular value decomposition to $D_j^k = U_j^k S_j^k (V_j^k)^T$. Thus, the rotation $R_{j\omega(k)}^k$ that transforms the vectors from the j coordinate system into the $\omega(k)$ coordinate system is: $R_{j\omega(k)}^k = U_j^k (V_j^k)^T$. That is, $\vec{\alpha}_{ij}^k = R_{j\omega(k)}^k \vec{z}_{ij}^k$. This gives us all vertices i from the j instances of component k in the same coordinate system.

In general, any frame can be chosen as reference frame, but the estimation of the skeleton becomes much easier if the chosen frame is close to the so-called zero position.

The input for the method is a set of conformed meshes, which should be as accurate as possible. Unfortunately, the initial generic model for the leg consists of only 536 vertices and we observed in our experiments that the approximation of the scanned data can be sometimes a little bit bumpy using this relatively sparse generic model. To solve this problem, the number of vertices (and triangular meshes) in the generic model can be increased by subdividing each triangular mesh into four. This results in 2091 vertices being available rather than 536, and 4076 triangles being available, rather than 1019.

Outlier Removal

After the previous step, as applied to each observed instance of a subcomponent, all instances j of a vertex $\vec{\alpha}_{ij}^k$ should lie close together. We expect that there will be some variation due to muscle shape changes and noise, but there might also be some outliers that will disrupt the next stage. These outliers will be distant from the other vertex instances. The result of the outlier detection is a modification to the vertex weights $\alpha_{ij}^k$. This might result in a vertex $\vec{\alpha}_{ij}^k$ being given a weight of 0, or simply just reduced according to its Mahalanobis distance $d_{ij}^k = d_M(\vec{\alpha}_{ij}^k, A_i^k \setminus \{\vec{\alpha}_{ij}^k\})$ with respect to the other instances of the vertex. $\alpha_{ij}^k = \alpha_{ij}^k$ if $d_{ij}^k < \sigma(A_i^k)$, otherwise, $$\alpha_{ij}^k = \alpha_{ij}^k \cdot \frac{1}{d_{ij}^k} \cdot \sigma(A_i^k) \quad (2)$$

where $\sigma(A_i^k)$ is the variance of the set of transformed subcomponent vertices $\vec{\alpha}_{ij}^k, j=[1 \ldots J]$.

Beside the re-weighting based on the estimated Mahalanobis distance, Eqn (2), the much more interesting (and time consuming) question is: What is the reliability of the conformed vertices that are neighbors to vertices which are weighted a-priori with $\alpha_{ij}^k=0$? Experiments have shown that the variance $\sigma$ of these vertices is bigger and consequently we assume a reduced accuracy. For this reason the weights of all vertices adjacent to unobserved areas is reduced by a half.

Fused Model Construction

Given the vectors $\vec{\alpha}_{ij}^k$ of corresponding vertices i of component k from conformed instance j, we wish to now form a point distribution model that describes the natural, non-random variations of these component instances. In order to correlate the motions of the points, we concatenate all of the coordinates to form a large vector and then look for correlated systematic variations in all vectors, by looking at the dominant eigenvectors of the covariance matrix of these vectors. This is essentially the Point Distribution Model (PDM) ([3], [4]) method. The algorithm used here varies slightly from the original PDM method in that the data values are weighted according to their confidence. This gives a more accurate initial covariance matrix.

Let $\vec{\alpha}_{i0}^k$ be the mean position of vertex i over all instances. Define $\vec{b}_{ij}^k = \vec{\alpha}_{ij}^k - \vec{\alpha}_{i0}^k$ as the variation vectors for vertex i. Construct a new vector $\vec{c}_j^k$ where the 3i-2, 3i-1, 3i components of the vector $\vec{c}_j^k$ are the x, y, z components respectively of $\alpha_{ij}^k \vec{b}_{ij}^k$. Similarly, construct a new vector $\vec{f}_j^k$ where the 3i-2, 3i-1, 3i components of the vector are $\vec{\alpha}_j^k$.

Construct the matrix $$C^k = \sum_j \vec{c}_j^k (\vec{c}_j^k)^T.$$

Construct the matrix $$F^k = \sum_j \vec{f}_j^k (\vec{f}_j^k)^T.$$

Construct the matrix $G^k = C^k/F^k$, on an entry-by-entry basis.

The matrix $G^k$ is a weighted estimate of the covariance matrix and can be factored by singular value decomposition to $G^k = P^k K^k (Q^k)^T$. The rows of matrix $Q^k$ give J eigenvectors $\vec{v}_l^k$, of which we use the first $L^k$ (or L if the number is independent of the component) associated with the least $L^k$ eigenvalues. Probably $L^k = 0, 1, 2$. With these, we then can form a parametric shape model. First, we unpack the eigenvectors $\vec{v}_l^k$ back into 3-vectors $\vec{\omega}_{il}^k$ for each vertex i. Then, we have the parametric model whose shape varies as a function of $L^k$ parameters $\mu_l^k$.

$$\vec{\delta}_i^k = \vec{a}_{i0}^k + \sum_l^{L^k} \lambda^k \mu_l^k \vec{\omega}_{il}^k \quad (3)$$

where $\mu_l^k$ is a deformation factor computed as a function of the joint angles (see next section) and $\lambda^k$ is a deformation exaggeration factor that enhances the shape variation away from the mean value. The unexaggerated value is $\lambda^k=1.0$ and typical over-exaggeration values are $\lambda^k=1.5$.

An alternative solution to the calculation of deformation, which accommodates misalignment during conformation and potential surface shear that may occur, can be defined such that variation is constrained to a single orthogonal direction (and not along $L^k$ eigenvectors) thus:

$$\vec{\delta}_i^k = \vec{p}_{i0}^k + \lambda^k \mu_i^k \vec{\phi}_i^k \quad (3A)$$

Where $\lambda^k$ is again the exaggeration factor to be applied and $\vec{p}_{i0}^k$ represents a mean axis point (on the normalized axis $X_j^k = \text{norm}(s_j^k - e_j^k)$ for start and end points of the skeletal component k) established from the average projections of vertices onto this axis across all instances J:

$$\vec{p}_{i0}^k = \frac{1}{J} \sum_j s_j^k + ((a_j^k - s_j^k) \cdot X_j^k) X_j^k$$

with $\vec{\phi}_i^k$ consequently defining the orthogonal unit vector extending from this mean point as:

$$\vec{\phi}_i^k = \frac{1}{J} \sum_j \frac{\vec{a}_{ij}^k - \vec{p}_{i0}^k}{\text{norm}(\vec{a}_{ij}^k - \vec{p}_{i0}^k)}$$

and $\mu_i^k$ derived as the variance of Euclidean distances (and not the projected distance which can be disrupted by rotational variation) from original vertices onto this orthogonal vector extending from the mean axis point, in relation to the joint angles $\vec{\phi}$:

$$\mu_i^k = \text{var}(\text{norm}(\vec{\alpha}_{ij}^k - \vec{p}_{i0}^k)) \vec{\phi}$$

In both cases, each vertex has a variable length displacement vector. As we have done this for all components k, we have a parametric model of the body components whose mean shape is an average of the J observed individual shapes. Each component model is expressed in its own local coordinate system.

While the mean shape as estimated above represents the weighted average shape for all subcomponents J over all instances, the shape parameters describe the variation of an individual shape relative to the estimated mean shape. While the estimation of the mean shape can be realized having only one or two good measurements per vertex, in order to get a reliable estimation of the shape deformation, more measurements per vertex with a sufficient variation are needed. With a typically available 3D data set, it may be that around 20% of the conformed vertices are observed in the scanning process twice or less. This problem can be obviated by either getting more observations, or modifying the configuration of the cameras in the 3D whole body scanner to get a better coverage.

Deformation Function Estimation

We hypothesize that the shape parameters $\mu_i^k$ are a function of the nearby joint angles and the gravity vector $\vec{g}$. Probably this really means only the joints at both ends that link the component to the rest of the body. The purpose of this step is to deduce a function that maps the joint angles $\vec{\phi}_j$ and $\vec{g}$ to the shape parameters $\mu_l^k$. We assume that the relationship is linear. The model we want is (assume that all joint angles and $\vec{g}$ are embedded in $\vec{\phi}$):

$$\vec{\mu}^k = H^k \vec{\phi} \tag{4}$$

The process has 2 steps:
1. Estimate the shape parameters $$\mu_{ij}^k = \frac{1}{V_k}(\vec{c}_j^k)^T \vec{v}_l^k$$

for each observed instance of the component by averaging the instances of the shape parameters projected onto the basis eigenvectors. We project the combined variation vectors $\vec{c}_j^k$ onto the combined basis vector set $\vec{v}_l^k$.

2. Compute the linear relationship $H^k$: Form matrix $E^k$ with the values $\mu_{ij}^k$ as the entry in column j and row l. Form matrix $F^k$ whose columns are the nearest $M^k$ joint angles $\vec{\phi}$ plus $R_{j\omega(k)}^k \vec{g}_j$. Then:

$$E^k = H^k F^k \tag{5}$$

where $$H^k = E^k (F^k)^T (F^k (F^k)^T)^{-1} \tag{6}$$

By assuming that only the nearby joints affect the function, we can eliminate the uninvolved joint angles from the equations above and thus reduce the number of observations needed to get a reasonable fit.

Subcomponent Relative Position Estimation

Assuming that the model consists of K subcomponents rigidly connected by joints, the following method is used to compute the average subcomponent relative position. Let $\vec{s}_j^k$ and $\vec{e}_j^k$ be the start and endpoints of a rigid skeleton of subcomponent k in view j. These are computed from the mesh vertices $\vec{y}_{ij}^k$ by estimating the characteristic 2D surface primitive. Because most of the subcomponents can be described best by ellipsoids, the estimation of the underlying skeleton is based on fitting an ellipsoid to all vertices $\vec{\alpha}_{ij}^k$ of the k-th subcomponent (see FIG. 1a). Thus, to define the skeleton, the main axes can be used.

If the ellipsoid fitted to the subcomponent has a specific characteristic shape, the axis to be used can be specified a-priori. Otherwise, $\vec{s}_j^k$ and $\vec{e}_j^k$ can be determined by estimating the closest intersection points between the axes of the approximating ellipsoid and the ellipsoids fitted to the vertices of the neighboring subcomponents. The resulting start and end points are illustrated in FIG. 1b.

Then, the average start and end points in the common reference frame are:

$$\vec{s}_{\omega(k)}^k = \frac{1}{J}\sum_j R_{j\omega(k)}^k (\vec{s}_j^k - \vec{y}_{0j}^k) \tag{7}$$

and $$\vec{e}_{\omega(k)}^k = \frac{1}{J}\sum_j R_{j\omega(k)}^k (\vec{e}_j^k - \vec{y}_{0j}^k) \tag{8}$$

We assume that: $\vec{e}_{\omega(k)}^k = \vec{s}_{\omega(k)}^{k+1}$. In the analysis below, we assume that all vectors and points are in the same common coordinate system $\omega(k)=\omega$. Otherwise, we would also need to include a rotation that maps from $\omega(k+1)$ to $\omega(k)$. We also define $\vec{\phi}^k$ as the vector of all joint angles, where $\phi_k$ is the k-th component of $\vec{\phi}^k$. Once start and end points of the rigid skeleton are estimated, a rotation function $T^k(\phi^k)$ is needed to transform local coordinates in subcomponent k+1's local coordinate system into subcomponent k's coordinate system (see FIG. 2).

The rotation $T^k(\phi^k)$ can be estimated using the Rodrigues formula:

$$T^k(\phi^k) = \cos\phi^k \cdot I + (1-\cos\phi^k) \cdot \vec{n}_\omega^k \cdot (\vec{n}_\omega^k)^T + \sin\phi^k \cdot (\vec{n}_\omega^k)^\wedge \tag{9}$$

where $\vec{v}_\omega^k = \vec{e}_\omega^k - \vec{s}_\omega^k$ is the axis orientation vector of the subcomponent k in the common reference frame. The axis vector is estimated by (we assume that consecutive axes are not parallel):

$$\vec{n}_\omega^k = \frac{\vec{v}_\omega^k \times \vec{v}_\omega^{k+1}}{|\vec{v}_\omega^k \times \vec{v}_\omega^{k+1}|} \tag{10}$$

and $$(\vec{n}_\omega^k)^\wedge = \begin{pmatrix} 0 & -n_\omega^k(z) & n_\omega^k(y) \\ n_\omega^k(z) & 0 & -n_\omega^k(x) \\ -n_\omega^k(y) & n_\omega^k(x) & 0 \end{pmatrix} \tag{11}$$

For estimating the joint angles of an observed instance of the joint, we use:

$$\phi^k = \arccos\left(\frac{\vec{v}_\omega^k \cdot \vec{v}_\omega^{k+1}}{|\vec{v}_\omega^k||\vec{v}_\omega^{k+1}|}\right) \tag{12}$$

When reconstructing instance of the object, we can use any desired value for $\phi^k$.

The estimation of the deformation function itself is based on the assumption that it is a function of the joint angles. Thus the deformation of one particular body part could be influenced by all joints. In our experiments we reduced the number of involved joints to two, the joints at the start and the end point $\vec{s}_k^k$ and $\vec{e}_k^k$ of the skeleton estimated for subcomponent k. All other joints are not considered to estimate the $\vec{\mu}^k$ but if knowledge about the muscle physiology ([5], [6]) is available the respecting joints can be simply included in the estimation of the deformation parameter, Eqn (4).

Complete Model Reassembly

The purpose of this step is to reposition the individual subcomponents k back into a combined coordinate system. Each deformable component model is estimated with the joint angle set to some value in the standard reference frame $\omega$. All deformations are expressed relative to the standard position. To reconstruct the model using the rotation given in Eqn (9), we need to rotate relative to the standard reference frame.

Let $\vec{\phi}_\omega$ be the joint angles in the standard reference frame. Let $T^0$ be the base subcomponent orientation and $\vec{s}_F^0$ be the starting point of the base subcomponent. Then the final global position $\vec{q}_F$ of point $\vec{q}_\omega^k$ of subcomponent k originally expressed in the standard coordinate system ω is given by:

$$\vec{q}_F^k = T^0 T^1(\phi^1 - \phi_\omega^1) \Lambda T^{k-1}(\phi^{k-1} - \phi_\omega^{k-1})(\vec{q}_\omega^k - \vec{s}_\omega^k) + \vec{s}_0^k \quad (13)$$

where $$\vec{e}_F^k = T^0 T^1(\phi^1 - \phi_\omega^1) \Lambda T^{k-1}(\phi^{k-1} - \phi_\omega^{k-1})(\vec{e}_\omega^k - \vec{s}_\omega^k) + \vec{s}_0^k \quad (14)$$

and $$\vec{e}_F^k = \vec{s}_F^{k+1} \quad (15)$$

Normally, $\vec{q}_\omega^k = \vec{\delta}_i^k$, the i-th deformed vertex of the k-th subcomponent. The final mesh results from the estimated mean shape combined with the pose specific shape variation.

Furthermore, the intersections of the reassembled vertices for overlapping subcomponents M need be calculated in order to collapse and simplify the unified complete model, thereby reducing surface artifacts at the overlap region by smoothing where two subcomponents meet. This is derived as the mean value:

$$\vec{q}_F^M = \frac{1}{M} \sum_m \vec{q}_F^m$$

Model Exaggeration

This occurs by varying the scaling factors $\lambda^k$ in equation (3) and (3A). Normally, there is a single scaling factor for each subcomponent k.

An example experimental implementation, and the results gained therefrom, shall now be described.

The data sets used for generating realistic body muscle deformation in the triangular mesh models were captured at The Edinburgh Virtual Environment Centre [7] using the 3D whole body scanner. The data that the 3D scanner produces is remarkably accurate under ideal conditions. However, ideal conditions are sometimes difficult to achieve, especially when scanning humans. The main problem is caused by the time needed to capture all views. Usually, it takes up to eight seconds in which the scanned objects ideally is in a fixed pose. Another problem is the compact architecture of the scanner where it is difficult or sometimes impossible to get a complete scan of a full body in arbitrary positions. And last but not least the accuracy of a scan may be affected by reflections caused by the mirrors mounted in the scanning chamber. The polygonal representation of the scanned data necessary in the conformation process was generated by using the Polyworks/Modeler software toolkit, [8].

Two examples of raw data patches are shown in FIG. 3a. The polygonal representation consists of ≈58 k 3D points and ≈120 k triangular patches. In the conformation process a generic model that consists of ≈2 k vertices and ≈4 k triangular patches, shown in FIG. 3b-c, is fitted to the raw data patches. The results of the conformation process are visualized in FIG. 4. The conformed raw data patches are the input for our method. In the middle column of FIG. 4 only the vertices and triangular meshes which are properly fitted to the raw data patches are shown. In our experiments up to 40% of all vertices of the generic model could not properly fitted to the raw data patches which means that these vertices $\vec{y}_{ij}^k, i \in [1 \ldots V_k]$, of the k-th subcomponent in instance j are weighted with a confidence value $\alpha_{ij}^k = 0$. Finally, the vertex normals are visualized in the right column where the direction of a vertex normal is color coded. The brighter color means that the vertex normal is pointing towards the observer's view point, and darker colored normals point away from the observer's view point. Even though one would expect that the vertex normals are orthogonal to the surface it is easy to see that it isn't the case. In fact, it seems the direction of the vertex normals is more or less arbitrary. In the merged result this is largely corrected.

Following Eqn (3), the shape can be described by as many shape parameters as measured vertices $\vec{\alpha}_{ij}^k$ belonging to subcomponent k. But, it is obvious that estimating all possible parameters is unnecessary and useless because most of them are zero or very small compared to the largest parameter. Thus, the number of estimated and used parameters can be limited a priori. In our experiments we estimated just two shape parameters for each subcomponent of each instance to give a very compact description of the body components. The final models (see FIG. 5) result from the estimated mean shape combined with the pose specific six shape parameters (two shape parameters per body part). Additionally, the vertex normals were estimated on the basis of an assumed Gouraud shading [9].

The final parametric model can be used for several purposes, for example, generating a smooth movement by interpolating between different key positions, or simply exaggerating the model shape by varying the shape parameter.

Beside the technical details of the proposed method the computational time needed to generate realistic body muscle deformation is of utmost importance. All functions have been implemented using the MATLAB software. The run time of the program is less than a minute on an AMD Athlon 1.5 GHz and an implementation of the algorithms using C/C++ suggests an acceleration around a factor 100.

Various modifications and improvements may be made to the above described embodiments without departing from the scope of the invention. In particular, the invention may be applied for the creation of models of other objects besides the human body. Furthermore, the specific experimental implementation can be varied. For example, the initial data scanning could use a different method and obtain data of different resolutions to that described, and the generic mesh used could equally be any applicable generic mesh to which the obtained range data can be fitted.

REFERENCES

The references referred to in the above description are as follows:

[1] P. Fua, R. Planners, and D. Thalmann. From synthesis to analysis: Fitting human animation models to image data. In *Proc. Computer Graphics International*, pp. 4-11, 1999.

[2] X. Ju and J. P. Siebert. Individualising human animation models. In *Eurographics*, 2001.

[3] T. F. Cootes, G. J. Edwards, and C. J. Taylor. Active appearance models. *IEEE Trans on Pattern Analysis and Machine Intelligence*, 23(6):681-685, 2001.

[4] T. F. Cootes, C. J. Taylor, and D. H. Cooper. Active shape models—their training and applications. *Computer Vision and Image Understanding*, 61(2), 1995.

[5] http://www.nlm.nih.gov/research/visible/visible human.html.

[6] Y. C. Fung. *Biomechanics: Mechanical Properties of Living Tissues*. Springer-Verlag, 1993.

[7] http://edvec.ed.ac.uk/.

[8] http://www.innovmetric.com/.

[9] H. Gouraud. Continuous shading of curved surfaces. *IEEE Trans on Computers*, 20(6):623-629, 1991.

What is claimed:

1. A method of generating a virtual model of an object, comprising the step of constructing a fused model to represent the variation of the shape of the object in a plurality of configurations, in which:
   position variation vectors are calculated which describe the variation of a plurality of points in the fused model from their mean positions over all the configurations of the object;
   the position variation vectors are assigned a weighting factor which represents a measure of their probabilistic confidence;
   a weighted covariance matrix is constructed to represent the variations;
   the weighted covariance matrix is operated on to obtain shape variation vectors representing the weighted direction and magnitude of variations;
   such that the fused model describes how the shape of the object varies as a function of the shape variation vectors scaled by a shape parameter, wherein the fused model is constructed from a conformed data set, obtained by performing the steps of:
      obtaining a set of range data from an object in a plurality of configurations;
      fitting the transformed range data to a generic model; and
      transforming the range data from each configuration to a common reference frame.

2. The method of claim 1, wherein the operation on the covariance matrix to get the shape variation vectors is a singular value decomposition, and the shape variation vectors are found by converting the eigenvectors of a factorized matrix into 3-vectors.

3. The method of claim 1, wherein the shape variation vectors are found by considering the variations as being constrained to a single vector orthogonal to a longitudinal axis of the object.

4. The method of any claim 1, wherein a function is calculated that maps the joint angles and gravity vector to the shape parameter.

5. The method of claim 4, wherein the function provides a linear relationship.

6. The method of claim 1, wherein the range data represents the object by defining a plurality of vertices, the positions of which are described by vectors.

7. The method of claim 1, wherein the generic model is a generic mesh model.

8. The method of claim 1, further comprising the step of performing a complete model reassembly, wherein the shape of the intersection between two reassembled subcomponents is accommodated as the mean of their shared vertices.

9. The method of claim 1, wherein the shape of the object in the fused model is further scaled by an exaggeration parameter.

10. The method of claim 9, wherein the exaggeration parameter defines a factor by which the magnitude of the modeled deformation of the object is multiplied.

11. The method of claim 1, wherein a plurality of objects forms a composite object and the relative positions of the objects are calculated so that a combined model can be constructed to represent the composite object.

12. The method of claim 11, wherein the objects are assumed to be rigidly connected by joints positioned at a start and an end position of each object:
   an axis is defined for each object which runs from a start position as averaged over all configurations to an end position as averaged over all configurations;
   the end point of one object is assumed to be commensurate with the start point of an adjacent object; and
   a complete model of the composite object is constructed in which the mean relative positions of the objects are combined with a specific configuration set, the set defining the specific configurations for each object in the composite object.

13. The method of claim 12, wherein a region of intersection between two adjacent rigid subcomponents defines an overlap region, the shape of which is derived as the mean shape.

14. The method of claim 12, wherein the axis is the main axis of an ellipsoid which is fitted to the fused model of the object, and the start and end points are determined from an estimation of the closest intersection points between the axes of the approximating ellipsoid and the ellipsoids fitted to the vertices of the neighboring objects.

15. The method of claim 14, wherein the composite object is part of a human body and the objects making up the composite object are parts of the body.

16. The method of claim 15, wherein the model is used to represent the deformation of muscle tissue in the body to create a virtual model of how a body deforms as it moves.

17. A model generation means to generate a virtual model of an object, comprising fused model construction means to construct a fused model suitable for modeling the variation of the shape of the object in a plurality of configurations, in which:
   position variation vectors are calculated which describe the variation of a plurality of points in the fused model from their mean positions over all the configurations of the object;
   the position variation vectors are assigned a weighting factor which represents a measure of their probabilistic confidence;
   a weighted covariance matrix is constructed to represent the variations;
   the weighted covariance matrix is operated on to obtain shape variation vectors representing the weighted direction and magnitude of variations; and
   such that the fused model describes how the shape of the object varies as a function of the shape variation vectors scaled by a shape parameter;
   said model generation means further comprising:
   data gathering means to obtain a set of range data from an object in a plurality of configurations;
   transformation means to transform the range data from each configuration to a common reference frame;
   and fitting means to fit the transformed range data to a generic model.

18. The model generation means of claim 17, wherein the fused model construction means further comprises singular value decomposition means suitable to operate on the covariance matrix, and eigenvector conversion means to convert the eigenvectors of a factorized matrix into 3-vectors, so as to find the shape variation vectors.

19. The model generation means of claim 17, wherein the fused model construction means further comprises means to derive a single vector orthogonal to a longitudinal axis of the object, to which the variations are constrained.

20. The model generation means of claim 17, wherein the range data represents the object by defining a plurality of vertices, the positions of which are described by vectors.

21. The model generation means of claim 17, wherein the generic model is a generic mesh model.

22. The model generation means of claim 17, being further suitable for performing a complete model reassembly wherein the shape of the intersection between two reassembled subcomponents is accommodated as the mean of their shared vertices.

23. A computer readable medium embodying data which is capable of co-operating with a computer apparatus to perform a method of generating a virtual model of an object, comprising the step of constructing a fused model to represent the variation of the shape of the object in a plurality of configurations, in which:
   position variation vectors are calculated which describe the variation of a plurality of points in the fused model from their mean positions over all the configurations of the object;
   the position variation vectors are assigned a weighting factor which represents a measure of their probabilistic confidence;
   a weighted covariance matrix is constructed to represent the variations;
   the weighted covariance matrix is operated on to obtain shape variation vectors representing the weighted direction and magnitude of variations;
   such that the fused model describes how the shape of the object varies as a function of the shape variation vectors scaled by a shape parameter;
   wherein the fused model is constructed from a conformed data set, obtained by performing the steps of:
   obtaining a set of range data from an object in a plurality of configurations;
   fitting the transformed range data to a generic model; and
   transforming the range data from each configuration to a common reference frame.

24. A computer readable medium embodying data which is capable of co-operating with a computer apparatus to form model generation means to generate a virtual model of an object, said model generation means comprising fused model construction means to construct a fused model suitable for modeling the variation of the shape of the object in a plurality of configurations, in which:
   position variation vectors are calculated which describe the variation of a plurality of points in the fused model from their mean positions over all the configurations of the object;
   the position variation vectors are assigned a weighting factor which represents a measure of their probabilistic confidence;
   a weighted covariance matrix is constructed to represent the variations;
   the weighted covariance matrix is operated on to obtain shape variation vectors representing the weighted direction and magnitude of variations; and
   such that the fused model describes how the shape of the object varies as a function of the shape variation vectors scaled by a shape parameter;
   said model generation means further comprising:
   data gathering means to obtain a set of range data from an object in a plurality of configurations;
   transformation means to transform the range data from each configuration to a common reference frame;
   and fitting means to fit the transformed range data to a generic model.

25. A computer generated virtual model of an object generated by constructing a fused model to represent the variation of the shape of the object in a plurality of configurations, in which:
   position variation vectors are calculated which describe the variation of a plurality of points in the fused model from their mean positions over all the configurations of the object;
   the position variation vectors are assigned a weighting factor which represents a measure of their probabilistic confidence;
   a weighted covariance matrix is constructed to represent the variations;
   the weighted covariance matrix is operated on to obtain shape variation vectors representing the weighted direction and magnitude of variations;
   such that the fused model describes how the shape of the object varies as a function of the shape variation vectors scaled by a shape parameter; and
   wherein the fused model is constructed from a conformed data set, obtained by performing the steps of:
   obtaining a set of range data from an object in a plurality of configurations;
   fitting the transformed range data to a generic model; and
   transforming the range data from each configuration to a common reference frame.

26. The virtual model of claim 25, provided on a computer usable medium.

* * * * *